# United States Patent [19]

Ensminger et al.

[11] Patent Number: 5,226,879
[45] Date of Patent: Jul. 13, 1993

[54] IMPLANTABLE ACCESS DEVICE

[75] Inventors: William D. Ensminger, 2770 Parkridge Dr.; James A. Knol, 1059 Hasper; James C. Andrews, 3568 River Pines, all of Ann Arbor, Mich. 48103; John J. Mastroeni, Pinckney, Mich.

[73] Assignees: William D. Ensminger; James C. Andrews; James A. Knol, Ann Arbor, Mich.

[21] Appl. No.: 818,626

[22] Filed: Jan. 10, 1992

Related U.S. Application Data

[63] Continuation-in-part of Ser. No. 654,661, Feb. 15, 1991, Pat. No. 5,180,365, which is a continuation-in-part of Ser. No. 539,793, Jun. 18, 1990, Pat. No. 5,053,013, which is a continuation-in-part of Ser. No. 487,541, Mar. 1, 1990, Pat. No. 5,057,084.

[51] Int. Cl.$^5$ .............................................. A61M 11/00
[52] U.S. Cl. ...................................... 604/93; 604/167; 604/256
[58] Field of Search ............... 604/93, 86, 167, 175, 604/256, 132, 131, 140, 141, 82, 83; 128/764, 769

[56] References Cited

U.S. PATENT DOCUMENTS

| | | |
|---|---|---|
| 3,288,137 | 1/1964 | Lund . |
| 3,402,710 | 9/1968 | Paleschuck . |
| 3,565,078 | 2/1971 | Vaillancourt et al. . |
| 3,699,956 | 10/1972 | Kitrilakis et al. . |
| 4,181,132 | 1/1980 | Parks . |
| 4,190,040 | 2/1980 | Schulte . |
| 4,230,109 | 10/1980 | Geiss . |
| 4,256,102 | 3/1981 | Monaco . |
| 4,387,879 | 6/1983 | Tauschinski . |
| 4,405,320 | 9/1983 | Cracauer et al. . |
| 4,425,119 | 1/1984 | Berglund . |
| 4,430,081 | 2/1984 | Timmermans . |
| 4,439,188 | 3/1984 | Dennehey et al. . |
| 4,447,237 | 5/1984 | Frisch et al. . |
| 4,464,178 | 10/1984 | Dalton . |
| 4,490,137 | 12/1984 | Moukheibir . |
| 4,491,126 | 1/1985 | Cullor . |
| 4,543,088 | 9/1985 | Bootman et al. . |
| 4,547,194 | 10/1985 | Moorhead . |
| 4,569,675 | 2/1986 | Prosl et al. . |
| 4,578,061 | 3/1986 | Lemelson . |
| 4,578,063 | 3/1986 | Inmann et al. . |
| 4,581,020 | 4/1986 | Mittleman . |
| 4,623,329 | 11/1986 | Drobish et al. . |
| 4,634,422 | 1/1987 | Kantrowitz et al. . |
| 4,645,495 | 2/1987 | Vaillancourt . |
| 4,650,473 | 3/1987 | Bartholomew et al. . |
| 4,673,394 | 6/1987 | Fenton, Jr. et al. . |
| 4,682,981 | 7/1987 | Suzuki et al. . |
| 4,692,146 | 9/1987 | Hilger . |
| 4,695,273 | 9/1987 | Brown . |
| 4,704,103 | 11/1987 | Stober et al. . |
| 4,710,167 | 12/1987 | Lazorthes . |
| 4,710,174 | 12/1987 | Moden et al. . |
| 4,712,583 | 12/1987 | Pelmulder et al. . |

(List continued on next page.)

Primary Examiner—John D. Yasko
Attorney, Agent, or Firm—Harness, Dickey & Pierce

[57] ABSTRACT

An infusion device which permits transcutaneous access to an implanted catheter for use in introducing an external filament such as a optical fiber, external catheter, guide wire or rigid needle. In accordance with this invention the device includes a valve assembly including a first valve element defining an aperture with a sealing member which is normally to engage and seal against the aperture. The sealing element is made from a hard material such as a metal. Upon introduction of a rigid external introducer such as a needle, the needle directly contacts the sealing member plug unsealing it from the valve element aperture which then closes against the external element. The device enables repeated access using a sharp introduced element such as a needle without it contacting soft sealing elements which could be degraded by such repeated access.

31 Claims, 3 Drawing Sheets

U.S. PATENT DOCUMENTS

| | | |
|---|---|---|
| 4,781,680 | 11/1988 | Redmond et al. |
| 4,781,693 | 11/1988 | Martinez et al. |
| 4,781,695 | 11/1988 | Dalton |
| 4,790,826 | 12/1988 | Elftman |
| 4,810,241 | 3/1989 | Rogers |
| 4,832,054 | 5/1989 | Bark .................... 604/93 X |
| 4,842,591 | 6/1989 | Luther |
| 4,857,053 | 8/1989 | Dalton |
| 4,886,501 | 12/1989 | Johnston et al. |
| 4,978,338 | 12/1990 | Melsky et al. ............ 604/86 X |
| 5,041,098 | 8/1991 | Loiterman et al. ........... 604/175 |

FOREIGN PATENT DOCUMENTS

| | | |
|---|---|---|
| 0119596 | 3/1984 | European Pat. Off. |
| 134745 | 8/1984 | European Pat. Off. |
| 3528878 | 2/1987 | Fed. Rep. of Germany |

OTHER PUBLICATIONS

Rational Drug Therapy, May, 1988, vol. 22, No. 5, William D. Ensminger M.D. and Ira S. Wollner, M.D.

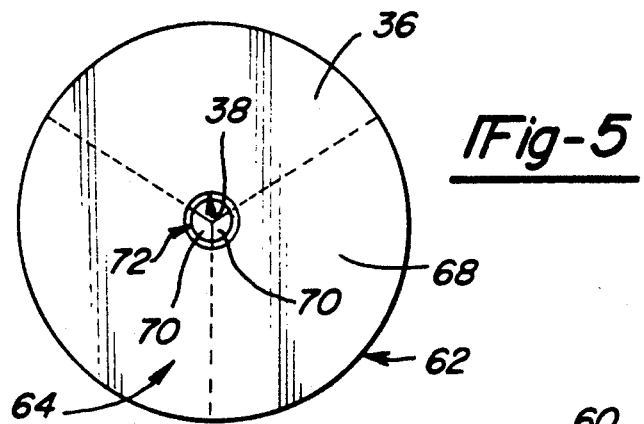
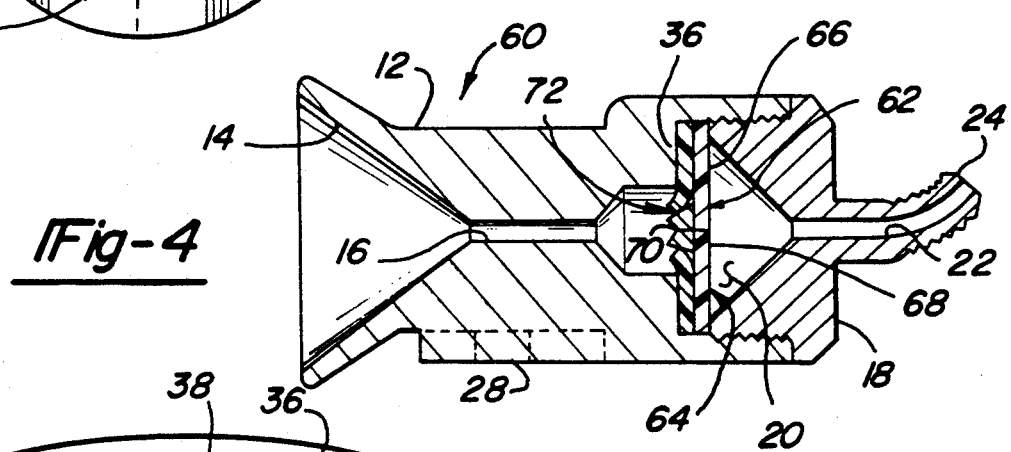
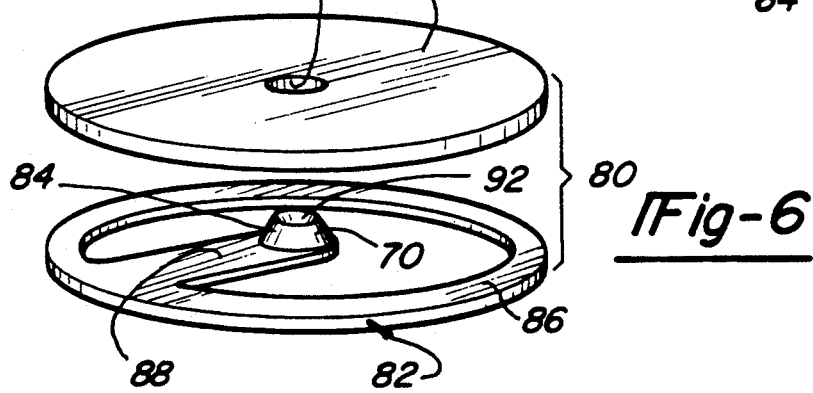
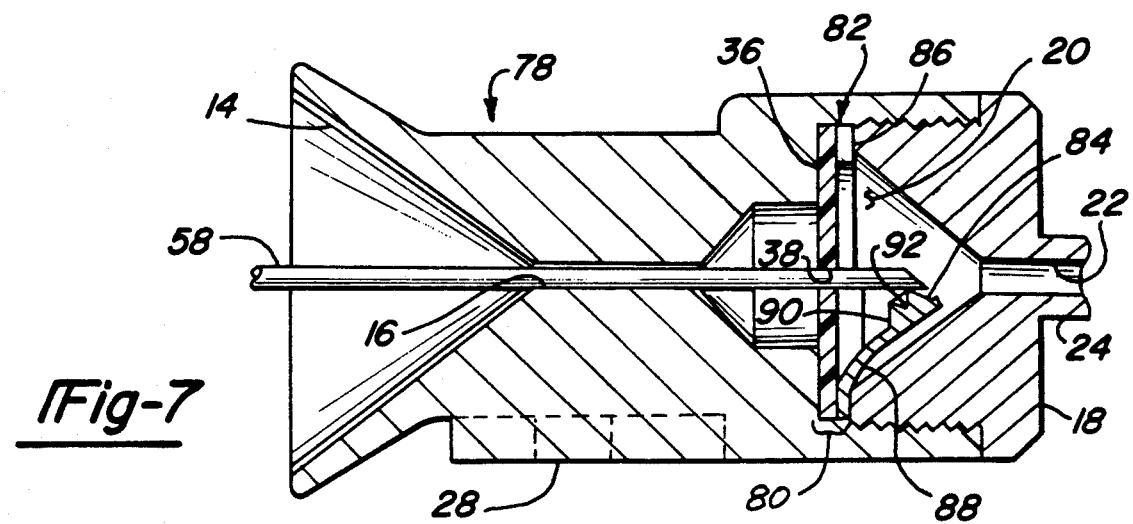

IMPLANTABLE ACCESS DEVICE

CROSS REFERENCE TO RELATED APPLICATIONS

This application is a continuation-in-part of U.S. application Ser. No. 654,661 filed on Feb. 15, 1991 entitled "Implantable Infusion Device" now U.S. Pat. No. 5,180,365 which is a continuation-in-part of U.S. Pat. application Ser. No. 539,793, filed Jun. 18, 1990, which issued as U.S. Pat. No. 5,053,013, which is a continuation-in-part of application Ser. No. 487,541, filed Mar. 1, 1990, which issued as U.S. Pat. No. 5,057,084.

BACKGROUND AND SUMMARY OF THE INVENTION

This invention is related to a patient access device and particularly to one which permits the introduction of an external filament such as a needle, external catheter, guide wire, or optical fiber transcutaneously.

This invention relates to a device to enable multiple patient access procedures including infusing a therapeutic agent to a desired site within a patient, feeding a filament to a desired internal site, or withdrawing a fluid from a patient; and more particularly, to such a device which is implanted such that no portion is transcutaneous. Its access portion is subcutaneous but designed so as to facilitate repeated access by the percutaneous route.

In current human and animal medical practice, there are numerous instances where therapeutic agents must be delivered to a specific organ or tissue within the body. An example is the infusion of chemotherapy into a central vein on a recurring basis over a lengthy treatment period for widespread sites of malignant tumor. Without an access device for intravenous drug infusion, multiple vein punctures over a lengthy period can result in progressive thrombosis, venous sclerosis, and destruction of small diameter peripheral vessels. In other cases, it may be desirable to infuse chemotherapy to a localized malignant tumor site. It may be difficult or impossible to deliver an agent specifically to such a site on a regular repetitive basis without surgically implanting an access system. Similarly, repeated arterial access is occasionally needed for injection of an X-ray dye or contrast agent into an artery for diagnostic purposes. In other situations, there is a need to remove a body fluid from a remote body site repetitively for analysis. Finally, sensing and physiological measuring devices incorporated into small diameter catheters and small diameter optical fibers are increasingly being utilized for monitoring body processes and could be more easily implemented through a properly designed access device with an adequate internal diameter.

In prior medical practice, percutaneous catheters have been used to provide vascular or organ access for drug therapy or removing body fluids. Although such systems generally performed in a satisfactory manner, numerous problems were presented by such therapy approaches, including the substantial care requirements by patients, e.g. dressing changes with sterile techniques, a significant rate of infection of the catheter because of its transcutaneous position, and a high rate of venous thrombosis, particularly if the catheter was located within an extremity vein.

Implantable infusion devices or "ports" have recently become available and are a significant advance over transcutaneous catheters. Presently available infusion ports have a number of common fundamental design features. The ports themselves comprise a housing which forms a reservoir which can be constructed from a variety of plastic or metal materials. A surface of the reservoir is enclosed by a high-density, self-sealing septum, typically made of silicone rubber. Connected to the port housing is an outflow catheter which communicates with a vein or other site within the patient where it is desired to infuse therapeutic agents. Implantation of such devices generally proceeds by making a small subcutaneous pocket in the patient under local anesthesia. The internal outflow catheter is tunnelled to the desired infusion site and is connected to the infusion port. When the physician desires to infuse or remove material through the port, a hypodermic needle is used which pierces the skin over the infusion port and is placed into the port.

Although presently available implantable infusion ports generally operate in a satisfactory manner, they have a number of shortcomings. Since these devices rely on a compressed rubber septum for sealing, there are limitations in the diameter of needles which can be used to penetrate the septum, since large diameter needles can seriously damage the septum. These diameter limitations severely restrict the flow rate of fluids passing through the port. Moreover, the needles used must be of a special design which minimizes septum damage.

For prolonged infusion using a conventional port, the infusion needle is taped to the patient's skin to hold it in position. Conventional ports do not allow the needle to penetrate deeply into the port; and consequently, a small displacement of the needle can cause it to be pulled from the port, allowing extravasation. In cases where locally toxic materials are being infused, extravasation of such materials can cause local tissue damage which can lead to a requirement for corrective surgery such as skin grafting or removal of tissue.

Presently available implantable infusion devices must also have a significant size to provide an acceptable target surface area for the physician who must locate the port and penetrate the septum properly with a needle. The port housing becomes bulky as the septum size increases since structure is required to maintain the septum in compression to provide self-sealing after the needle is removed. Moreover, presently available infusion ports are difficult to clear if thrombosis occurs within them or in the implanted outflow catheter, since it is difficult if not impossible to feed a cleaning wire through the penetrating hypodermic needle in a manner which will clear the infusion device and the internal outflow catheter. Present infusion ports have a space which contains a retained fluid volume beneath the self-sealing septum which increases the volume of drug which must be administered to enable a desired quantity to reach the infusion site. This retained volume also poses problems when a physician desires to deliver different drugs to the same infusion site which are incompatible or rendered less effective when mixed. In addition, when it is desired to withdraw blood through the port, the retained volume of the prior art infusion ports is an area where blood clotting can occur, thus interfering with future access to the site. And finally, for present infusion ports, there is a risk that the physician attempting to pierce the port septum will not properly enter it, leading to the possibility of extravasation which can cause significant undesirable consequences as mentioned previously.

In applicants' related patent application and issued patents, various approaches toward permitting transcutaneous access to implanted catheter are described. In accordance with those devices, multiple sealing members are used to provide an adequate fluid seal across the access device, both when an external filament is introduced into the device and after it is removed. The access ports in accordance with this invention achieve simplicity in construction and reduce the number of components necessary to provide the necessary fluid seal. In those applications where it is desired to access a port using a sharp needle, damage to elastomeric sealing elements can occur over repeated entries to the port in prior port designs. In accordance with this invention, the implanted port has an articulating valve mechanism in which the accessing needle (or other filament) contacts a hard material such as a metal to open the valve. Accordingly, a durable device is provided which is not damaged through long term use.

The features of the present invention are primarily achieved through use of a valve assembly in which a sealing element is normally maintained in contact with a valve seat. When introducing an external filament, which may be a needle, catheter, wire, optical fiber etc., the filament engages the sealing element forcing it from engagement with the valve seat. Once fully inserted into the access device, features are provided to assure a fluid seal around the introduced filament.

Additional benefits and advantages of the present invention will become apparent to those skilled in the art to which this invention relates from the subsequent description of the preferred embodiments and the appended claims, taken in conjunction with the accompanying drawings.

BRIEF DESCRIPTION OF THE DRAWINGS

FIG. 4 is a cross-sectional view through an access port according to a second embodiment of this invention showing a valve assembly comprising metal seal elements affixed to a multi-leaf elastomeric valve disk.

FIG. 5 is a frontal view of the valve assembly of the port shown in FIG. 4.

FIG. 6 is an exploded pictorial view of a valve assembly in accordance with a third embodiment of this invention incorporating a unitary seal member for sealing against the valve seat formed by a sealing disk.

FIG. 7 is a cross-sectional view of an access port incorporating the valve assembly shown in FIG. 6 and further showing an accessing needle penetrating the device.

DETAILED DESCRIPTION OF THE INVENTION

Figure 1:
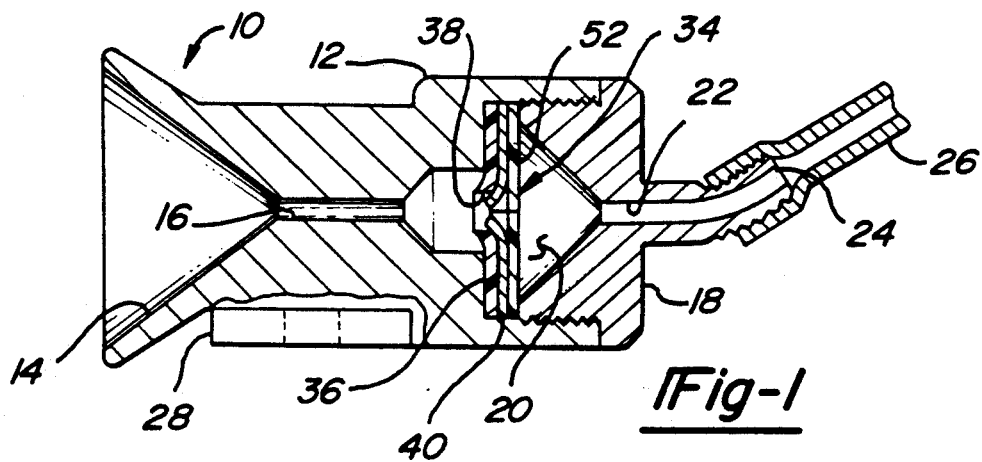
FIG. 1 is a cross-sectional view through an access port in accordance with a first embodiment of this invention shown in a normal condition in which an external filament is not present within the device.
Figure 2:
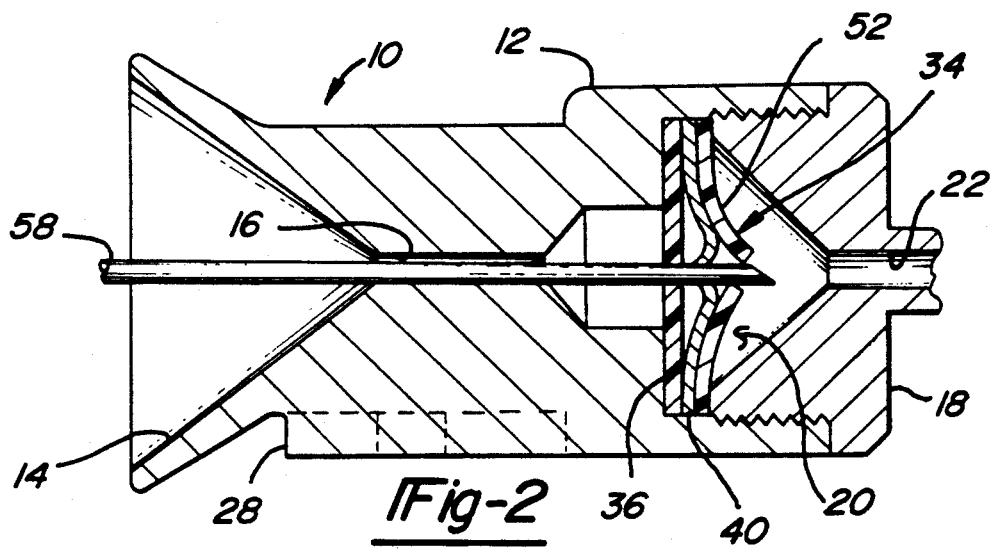
FIG. 2 is a somewhat enlarged cross-sectional view of the access port of FIG. 1 shown with an accessing needle penetrating the device.

An access device in accordance with this invention is shown in FIGS. 1 and 2, and is generally designated by reference number 10. As shown, access port 10 is similar to that described in applicant's issued U.S. Pat. Nos.: 5,053,013 and 5,057,084, to which the present application is related. Access port 10 is designed to allow a sharp needle to access the device for purposes including infusing drugs or other fluids in the patient or withdrawing fluids from the patient. Access port 10 generally has housing 12 which defines a generally funnel shaped entrance orifice 14. Entrance orifice 14 has a decreasing cross-sectional area which ends at housing passageway 16. The shape of entrance orifice 14 serves to guide a needle into passageway 16. To that end, the surface of housing 12 forming orifice 14 is a hardened material such as titanium which has been found to be acceptable for this application.

Housing 12 together with outlet plug 18 define valve chamber 20 located between passageways 16 and 22. As shown, the protruding catheter connector tube 24 of outlet plug 18 is bent to provide a positive means for preventing an introduced needle from passing entirely through the device and potentially damaging a soft elastomeric implanted catheter 26. Connector tube 24 does, however, permit more flexible filaments such as a catheter, guide wire or optical fiber to pass into implanted catheter 26. Mounting pad 28 enables the device to be conveniently mounted to subcutaneous support tissue preferably using sutures, staples, or other fasteners.

Figure 3:
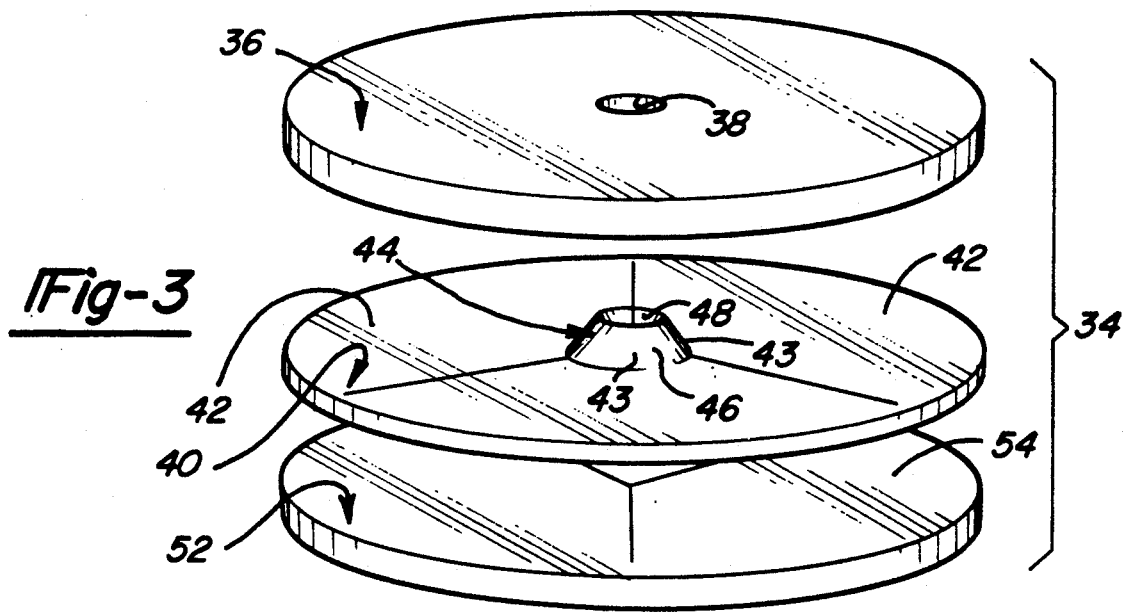
FIG. 3 is an exploded pictorial view of the valve assembly of the port shown in FIGS. 1 and 2.

Valve assembly 34 is disposed within valve chamber 20 and is best described with reference to FIG. 3. Valve disk 36 is made from an elastomeric material such as silicone rubber and is positioned in valve chamber 20 closest to entrance orifice 14. Disk 36 has a central aperture 38 defining a valve seat which is intended to seal against the introduced needle or filament upon insertion into access port 10, as will be described in more detail as follows. Stacked directly against disk 36 is sealing member 40 which is preferably made, at least partially, of a hard material such as a metal. Sealing member 40 as shown in FIGS. 1, 2 and 3 is a circular metal disk having three cuts intersecting at the center of the disk and extending radially to the outer perimeter but stopping short of the perimeter, thus defining three separate cantilever supported leaves 42. Each of leaves 42 is locally deflected from the plane of the disk at the disk center to define a segment 43 which combine to define conical sealing plug 44. Plug 44 has an external generally conical surface 46 with its center defining a concave surface 48. Sealing member 40 can be made from a flat sheet metal stock which is locally deflected at the center area to define plug 44. Alternatively, the disk can be machined or cast such that the plug 44 is defined by a locally thickened region of the disk.

Valve assembly 34 also incorporates an additional leaflet valve element 52 formed from a flat sheet of elastomeric material. Valve element 52 defines radial cuts which join at the geometric center of the disk, defining separate valve leaves 54.

As shown in FIGS. 1 and 2, the three elements comprising valve assembly 34 namely, valve disk 36, sealing member 40 and leaflet valve 52 are stacked directly against one another and are trapped in position between access port housing 12 and outlet plug 18. As shown in the Figures, housing 12 defines a relatively small diameter passageway on the side of valve assembly 34 closest to entrance passageway 16. In this manner, seal element 36 is constrained against deflecting toward entrance orifice 14 except at near its central area defining aperture 38. On the opposite side of valve assembly 34, outlet plug 18 defines a large diameter area for the deflection of the leaves of valve elements 40 and 52.

The operation and cooperation of the elements defining access port 10 will now be described with particular reference to FIGS. 1 and 2. FIG. 1 shows the configuration of valve assembly 34 when access port 10 is in its normal condition, implanted within the patient and not being used for access. In that condition, the segments of sealing member 40 making up sealing plug 44 project into and seal against disk aperture 38 which acts as a valve seat. Plug 44, having a conical outside surface 46, presses against disk aperture 38, causing it to be stretched and enlarged. Due to the contact between disk 36 and sealing member 40, a seal against fluid leakage is provided.

Leaflet valve element 52 is provided to enhance the level of sealing by preventing fluid leakage between sealing member leaves 42. In the normal condition of the device as shown in FIG. 1, the valve leaves 54 meet to provide a fluid seal. As shown in FIG. 3, as a means of providing enhanced fluid sealing, the orientation of the cuts defining leaflet valve leaves 54 and the cuts defining the individual sealing member leaves 42 are off-set or indexed so that they are not in registry.

FIG. 2 shows the orientation of the elements of access port 10 upon insertion of accessing external needle 58. Housing orifice 14 and passageway 16 serve to direct and orient needle 58 such that the sharp point of the needle strikes concave surface 48 of plug 44. Due to the enlargement of valve disk aperture 38 through its interaction with plug 44, the sharp point of the needle does not strike valve disk 36. As needle 58 is forced through the device, sealing member leaves 42 are forced to deflect in the direction of the outlet plug passageway 22. This movement of leaves 42 causes the segments defining plug 44 to move from engagement with disk aperture 38 which is allowed to contract in diameter. The undeformed diameter of aperture 38 is selected so that it will form a fluid seal against needle 58 (or another introduced filament such as a catheter around the needle which can be left in the device after the needle is removed). Continued deflection of leaves 42 allows free passage of the needle 58. Such deflections also causes valve leaves 54 to separate, allowing passage of needle 58 but without being damaged by contact with the needle point.

As is evident from the above description of the operation of access port 10, repeated access using needle 58 will not damage the device since the needle repeatedly strikes the hard material forming plug 44. Access port 10 also permits the introduction of the external filaments, such as an external catheter, optical fiber or guide wire, provided that it has sufficient rigidity to deflect the valve elements in the manner previously described. Access port 10 could also enable external filaments to be introduced via needle 58 either as fed through its center passageway, or introduced around the needle like a typical angiography catheter.

FIG. 4 illustrates an access port 60 incorporating a valve assembly 62 in accordance with the second embodiment of this invention. This embodiment, along with those described elsewhere in this specification have elements and features identical to those of the first embodiment, and are identified with like reference numbers. FIG. 5 illustrates valve assembly 62 which includes a valve disk 36 identical to that previously described. The distinction of this embodiment over valve assembly 34 is that the sealing member 64 which defines plug 70 is a composite structure. Sealing element 64 is formed from an elastomeric or flexible base disk 66 having a number of radically projecting cuts defining individual leaves 68 as in the case of sealing member 40 described previously. Attached to leaves 68 near the center of base disk 66 are plug segments 70 which together define a sealing plug 72 as in the prior embodiment which are made of a hard material such as a metal. Plug elements 70 are bonded or otherwise structurally affixed to disk 66.

In use, valve assembly 62 operates in a manner consistent with the description of valve assembly 34. A principle advantage of the configuration of valve assembly 62 is that sealing element disk 66 performs the combined functions of sealing as with the leaflet valve element 52 of the first embodiment, and further supports plug segments 70.

FIGS. 6 and 7 illustrate an access port 78 in accordance with a third embodiment of this invention. Access port 78 has valve assembly 80 with a valve disk 36 identical to that present in the first and second embodiments. In this embodiment, however, sealing member 82 is a unitary structure which includes plug element 84 attached to a mounting ring 86 via a cantilever arm 88. As with the prior embodiments, plug 84 defines an external conical surface 90 and a central concave surface 92. In this design, however, the plug 84 is a unitary element.

In operation, valve assembly 80 operates as like those of the prior embodiments in that in a normal condition without an external filament inserted within the access device, plug 84 is in sealing engagement with disk aperture 38. Upon the introduction of an external filament such as needle 58, engagement between the needle and sealing plug 84 urges it out of engagement with disk aperture 38, and deflects it sufficiently to allow passage of the needle, as shown in FIG. 7. This process also results in the contraction of the diameter of aperture 38, causing it to constrict around the introduced filament. A significant benefit of valve assembly 80 results from the fact that plug 84 is a unitary structure and, therefore, does not provide a fluid leakage path. In the normal condition with plug 84 against disk aperture 38, a fluid seal is provided, and therefore, additional sealing elements such as a leaflet valve 52 shown in the first embodiment are unnecessary.

Figure 8:
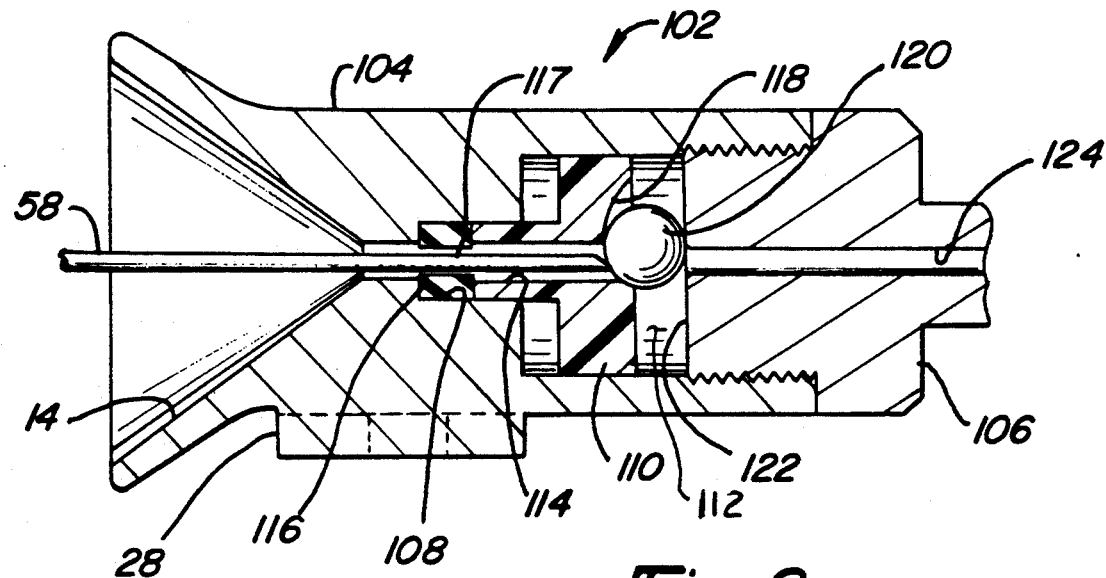
FIG. 8 is a cross-sectional view taken through an access port in accordance with a fourth embodiment of this invention shown with an accessing needle partially penetrating the device.
Figure 9:
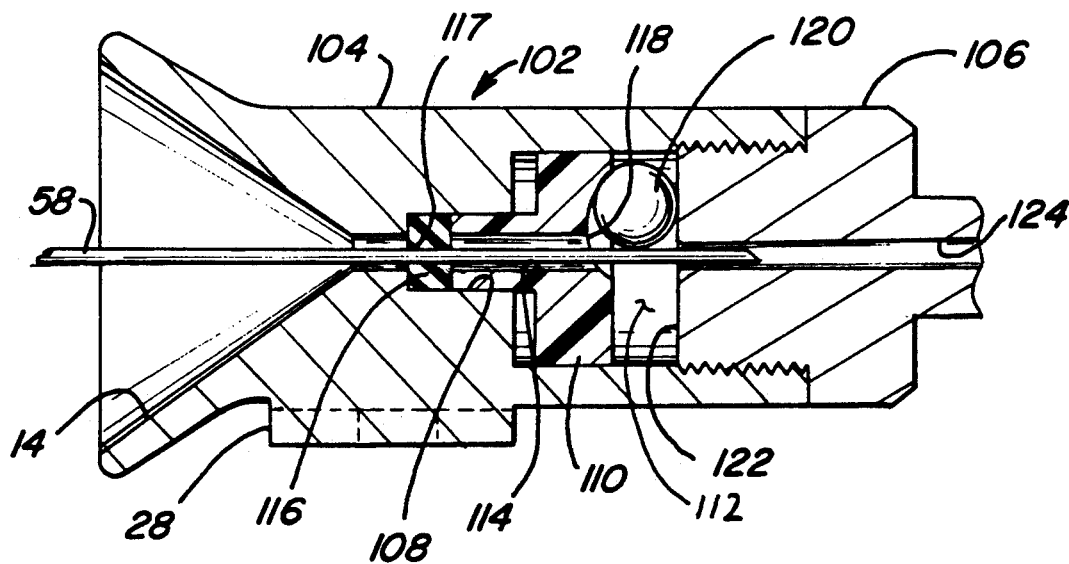
FIG. 9 is a cross-sectional view of the access port shown in FIG. 8 but showing the accessing needle penetrating the valve assembly to permit access to an implanted catheter.

FIGS. 8 and 9 provide an illustration of access port 102 in accordance with a fourth embodiment of this invention. This embodiment features a modified housing 104 and outlet plug 106. Housing 104 forms a small diameter counterbore 108 extending toward entrance orifice 14. Piston element 110 is positioned within housing cavity 112 and includes a central filament passageway 114. Piston 110 butts against elastomeric bushing 116 having passageway 117, which is trapped within counterbore 108. The head of piston 110 forms a dished concave surface 118 which supports valve ball 120. Piston surface 118 is formed to position ball 120 such that it is displaced from alignment with piston passageway 114. Outlet plug 106 forms a generally flat surface 122 within housing cavity 112 which provides for movement of ball 120, as is described in more detail below.

Operation of access port 102 will be described with reference to FIGS. 8 and 9. FIG. 8 represents the orientation of the elements comprising the device while inserting access needle 58. As is shown in FIG. 8, access needle 58 engages ball 120 off-center. Continued insertion of needle 58 causes ball 120 to be displaced upward to the position shown in FIG. 9. During such displacement, piston 110 is caused to move toward entrance orifice 14 as ball 120 "rides out" of concave surface 118. This displacement of piston 110 compresses bushing 116. Since bushing 116 is trapped within counterbore 108 its axial compression causes bushing passageway 117 to constrict, thus causing it to seal against the introduced needle or other filament. As shown in FIG. 9, once ball 120 is fully displaced, free passage to the exit passageway 124 is provided. When needle 58 is completely removed from the device, ball 120 reseats in position within concave surface 118 which provides a fluid seal. It would be possible to enhance the fluid seal provided by ball 120 in its normal position by providing an O-ring or other elastomeric valve seat (not shown) installed either on outlet plug 106 or a piston 110 and engaging the ball.

While the above description constitutes the preferred embodiments of the present invention, it will be appreciated that the invention is susceptible of modification, variation and change without departing from the proper scope and fair meaning of the accompanying claims.

We claim:

1. An implantable access port to permit the introduction of an external filament such as an external catheter, needle, guide wire or optical fiber within a patient comprising:
   a housing defining a generally funnel shaped entrance orifice, an entrance passageway and an exit passageway, said entrance orifice for guiding said external filament into said housing entrance passageway and an exit passageway,
   an elastomeric valve element disposed within said housing between said entrance and exit passageways defining an aperture for permitting the passage of said external filament therethrough,
   sealing means for defining a plug which is urged into sealing engagement with said valve element aperture, said plug being forced from sealing engagement with said aperture upon contact with said external filament as said external filament is introduced into said port through said entrance passageway, and
   mounting means formed by said housing for enabling fastening of said housing subcutaneously.

2. An implantable access port according to claim 1 wherein said plug is shaped to extend partially through and expand valve element aperture when said external filament is not within said housing and wherein said valve element aperture constricts into sealing engagement with said external filament upon said plug being forced from sealing engagement with said aperture.

3. An implantable access port according to claim 2 wherein said plug defines a convex outer surface which aids in expanding said valve element aperture.

4. An implantable access port according to claim 1 wherein said aperture is circular.

5. An implantable access port according to claim 1 wherein said housing entrance passageway is oriented with respect to said plug whereby upon introduction of said external filament, said filament contacts said plug and is prevented from contacting said sealing element while said plug is in said sealing engagement with said valve element aperture.

6. An implantable access port according to claim 5 wherein said plug defines a concave central area which is engaged by said external filament.

7. An implantable access port according to claim 1 wherein said plug is formed of a metal.

8. An implantable access port according to claim 1 wherein said sealing means comprises a disk having plural leaves with each having plug segments at near the center of said disk which together define said plug.

9. An implantable access port according to claim 8 wherein said sealing means disk is made of metal and wherein said plug segments are formed integrally by said disk.

10. An implantable access port according to claim 8 wherein said plug segments are formed by separate metal elements bonded to a substrate.

11. An implantable access port according to claim 1 wherein said sealing member plug is supported by an arm urging said plug into engagement with said valve element aperture.

12. An implantable access port according to claim 1 further comprising a second elastomeric valve element disposed in engagement with said sealing means and positioned adjacent said exit passageway.

13. An implantable access port according to claim 12 wherein said second elastomeric valve element comprises a leaflet valve having plural leaves which join near the center of said valve.

14. An implantable patient access port to permit the introduction of a needle for the removal or introduction of a fluid through an implanted catheter, or permitting the introduction of a filament such as an external catheter, guide wire or optical fiber, comprising:
    a housing defining a generally funnel shaped entrance orifice for guiding said needle into a housing entrance passageway, said housing further having an exit passageway with a valve chamber within said housing between said entrance and exit passageway, said housing further having means for connecting said passageway to said implanted catheter,
    an elastomeric valve element positioned within said valve chamber adjacent said housing entrance passageway, and having a generally round aperture located in alignment with said housing entrance passageway.
    sealing means for defining a plug which is normally biased into sealing engagement with said valve element aperture and enlarging said aperture, said plug being formed of a hard material for enabling repeated engagement with said needle, said plug projecting toward said housing entrance passageway whereby insertion of said needle or said filament and engagement with said plug forces said plug to deflect out of said aperture and allowing said valve member aperture to constrict into sealing contact with said needle or said filament, and
    mounting means formed by said housing enabling fastening of said housing subcutaneously.

15. An implantable access port according to claim 14 wherein sad housing passageway is oriented with respect to said plug whereby upon introduction of said needle or said external filament, said needle or said filament contacts said plug and is prevented from contacting said sealing element while said plug is in said sealing engagement with said sealing element aperture.

16. An implantable access port according to claim 14 wherein said plug defines a concave central area which is engaged by said needle or said external filament.

17. An implantable access port according to claim 14 wherein said plug is formed of a metal.

18. An implantable patient access port according to claim 14 wherein said sealing member comprises a disk having plural leaves which join at near the center of said disk to define said plug.

19. An implantable access port according to claim 18 wherein said plug is defined by a plug segment disposed at the center region of each of said leaves.

20. An implantable access port according to claim 18 wherein said sealing means disk is made of metal and wherein said plug segments are formed integrally by said disk.

21. An implantable access port according to claim 18 wherein said plug segments are formed by separate metal elements bonded to a substrate.

22. An implantable access port according to claim 14 wherein said sealing member plug is supported by an arm urging said plug into engagement with said valve element aperture.

23. An implantable access device according to claim 14 wherein said plug defines a convex shaped outer surface with a central region defining a concave disk.

24. An implantable access device according to claim 14 further comprising a second elastomeric valve element disposed in engagement with said sealing means and positioned adjacent said exit passageway.

25. An implantable access device according to claim 24 wherein said second elastomeric valve element comprises a leaflet valve having plural leaves which join near the center of said valve.

26. An implantable access port to permit the introduction of an external filament such as an external catheter, needle, guide wire or optical fiber within a patient comprising:
   a housing defining a generally funnel shaped entrance orifice for guiding sad external filament into a housing entrance passageway, said housing further defining an exit passageway and a valve chamber positioned between said passageways,
   a sealing ball element disposed within said valve chamber,
   a valve member disposed in said housing valve chamber defining a ball seat wherein when said ball rests on said ball seat, fluid flow between said entrance and exit passageways is inhibited, said ball seat positioning said ball such that said external filament engages said ball and displaces said ball from sealing contact with said ball seat thereby allowing said external filament to enter said exit passageway, said ball being resiliently biased into engagement with said seat when said external filament is removed.

27. An implantable access device according to claim 26 wherein said ball seat positions said ball off-center with respect to the axis of said entrance and exit passageways.

28. An implantable access device according to claim 26 wherein said ball seat is defined by a piston member which is resiliently biased by an elastomeric biasing member.

29. An implantable access device according to claim 28 wherein said piston member is caused to be displaced toward said entrance orifice upon said ball being displaced allowing passage of said external filament.

30. An implantable access device according to claim 29 wherein said elastomeric biasing member comprises a bushing having a central passageway through which said external filament passes upon introduction of said filament and wherein compression of said bushing caused by displacement of said ball causes said central passageway to constrict into sealing engagement with sad external filament.

31. An implantable access port to permit the introduction of an external filament such as an external catheter, needle, guide wire or optical fiber within a patient comprising:
   a housing defining a generally funnel shaped entrance orifice, an entrance passageway and an exit passageway, said entrance orifice for guiding said external filament into said housing entrance passageway and an exit passageway,
   valve means disposed within said housing valve chamber having an elastomeric sealing element defining an aperture through which said filament passes, and having an actuating element which causes said aperture to constrict around said filament after said filament has been introduced into said housing.

* * * * *

UNITED STATES PATENT AND TRADEMARK OFFICE
CERTIFICATE OF CORRECTION

PATENT NO. : 5,226,879
DATED : July 13, 1993
INVENTOR(S) : William D. Ensminger et al.

It is certified that error appears in the above-identified patent and that said Letters Patent is hereby corrected as shown below:

Column 8, Line 65, Claim 15 after "wherein" delete "sad" and insert --said--.

Column 9, Line 43, Claim 26 after "guiding" delete "sad" and insert --said--.

Signed and Sealed this

Twenty-second Day of March, 1994

Attest:

BRUCE LEHMAN

*Attesting Officer*   *Commissioner of Patents and Trademarks*